United States Patent [19]
Carter et al.

[11] Patent Number: 5,879,706
[45] Date of Patent: Mar. 9, 1999

[54] VALACICLOVIR TABLETS CONTAINING COLLOIDAL SILICON DIOXIDE

[75] Inventors: Barry Howard Carter, Kinston, N.C.; Lloyd Gary Tillman, Carlsbad, Calif.

[73] Assignee: Glaxo Wellcome Inc., Research Triangle Park, N.C.

[21] Appl. No.: 875,172

[22] PCT Filed: Jan. 19, 1996

[86] PCT No.: PCT/GB96/00111

§ 371 Date: Aug. 29, 1997

§ 102(e) Date: Aug. 29, 1997

[87] PCT Pub. No.: WO96/22082

PCT Pub. Date: Jul. 25, 1996

[30] Foreign Application Priority Data

Jan. 20, 1995 [GB] United Kingdom .................... 9501127

[51] Int. Cl.⁶ .................................................... A61K 9/28
[52] U.S. Cl. .................... 424/464; 424/465; 424/474; 514/770; 514/772; 514/772.3; 514/781; 514/934
[58] Field of Search .................... 424/464, 465, 424/474, 441, 480

[56] References Cited

U.S. PATENT DOCUMENTS 5,556,639  9/1996  Fielden .................................... 424/480

FOREIGN PATENT DOCUMENTS

| | | |
|---|---|---|
| B-16498/92 | 12/1992 | Australia . |
| 0 196 546 B1 | 10/1986 | European Pat. Off. . |
| 0 308 065 | 3/1989 | European Pat. Off. . |
| 0 349 103 | 1/1990 | European Pat. Off. . |
| WO 92/19227 | 11/1992 | WIPO . |

OTHER PUBLICATIONS

Chemical Abstracts, vol. 118, No. 10, Mar. 1993 Abstract No. 87553 & Zhongguo vol. 23, No. 8, 1992 p. 350–1 Yuan "Improved Preparation of Ibuprofen Tablets".

Chemical Abstracts vol. 69, No. 4, Jul. 1968 Abstract No. 11048 & SB. TR., VSes. Nauch.–Issled, Inst. Nov. Stroit. Mater. vol. 15, 1967 pp. 15–21 Edell'man, "Effect of the nataure and particles size of fillers and methods etc.".

Chemical Abstracts, vol. 95, No. 2, Jul. 1981 Abstract No. 12656 & Pharmazie vol. 36, No. 1, 1981 p. 32–4 lonchev, KH., Velikova, E "Optimization of the composition of a multicomponent pharmaceutical form etc.".

Chemical Abstracts, vol. 102, No. 18, May 1985 Abstract No. 154736 & J. Pharm. Pharmacol. vol. 37, No. 3, 1985 p. 193–5 Esezobo "The effect of some excipients on the physical properties of a paracetamol tablet formulation".

Farmatsiya, vol. 35, No. 4, 1986 p. 25–8 "Study of the Possibility of Producing Celanide Tablets etc.".

J. Pharm. Pharmacol 1986 36:51–54 Johansson et al Investigation of the film formation of Magnesium etc.

Drug Development and Industrial Pharmacy 6(6) 573–89 (1980) Bossert et al "Effect of Mixing on the Lubrication of Crystlaline Lactose by Magnesium Stearate".

Pharm. Acta Helv. 52 No. 3 (1977) p. 33–9 Lerk et al "Interaction of lubricants and colloidal silica during etc.".

Pharm. Acta Helv. 52 No. 3 (1977) pp. 39–44 Lerk et al "Interaction of lubricants and colloidal silica during etc".

(List continued on next page.)

Primary Examiner—Thurman K. Page
Assistant Examiner—James M. Spear
Attorney, Agent, or Firm—Nixon & Vanderhye

[57] ABSTRACT

A tablet comprising at least 50% w/w valaciclovir and 0.05 to 3% w/w colloidal silicon dioxide in which the valaciclovir is present within granules of the tablets and the silicon dioxide, a lubricant and a microcrystalline cellulose filler are present extragranularly has excellent hardness and friability properties while still maintaining lubrication of the tablet granules.

28 Claims, 3 Drawing Sheets

OTHER PUBLICATIONS

Ahmed et al Int. J. Pharm. 41 (1953) 223–6 Tablet re Toughening effects of Colloidal Silica etc.

Ragnarsson et al Int J. Pharmaceutics 1979 pp. 127–131 The Influence of Mixing Time and Colloidal Silica etc.

Antiviral Chemistry & Chemotherapy (1992) 3 (3) 157–164 Beauchamp et al "Amino acid ester prodrugs of acyclovir".

Handbook of Pharmaceutical Excipients 1994 p. 253–6 Colloidal Silicon Dioxide.

USP (1995) p. 1840 (911 Viscosity/Physical Tests p. 2300 Colloidal Silicon Dioxide (1216) Tablet Friability.

Pharmaceutical Dosage Forms: Tablets vol. 1 pp. 183–185 Lieberman Compressed Tablets Jan. 1995.

Silver Platter v 2.12 IPA 1970–Sep. 1994.

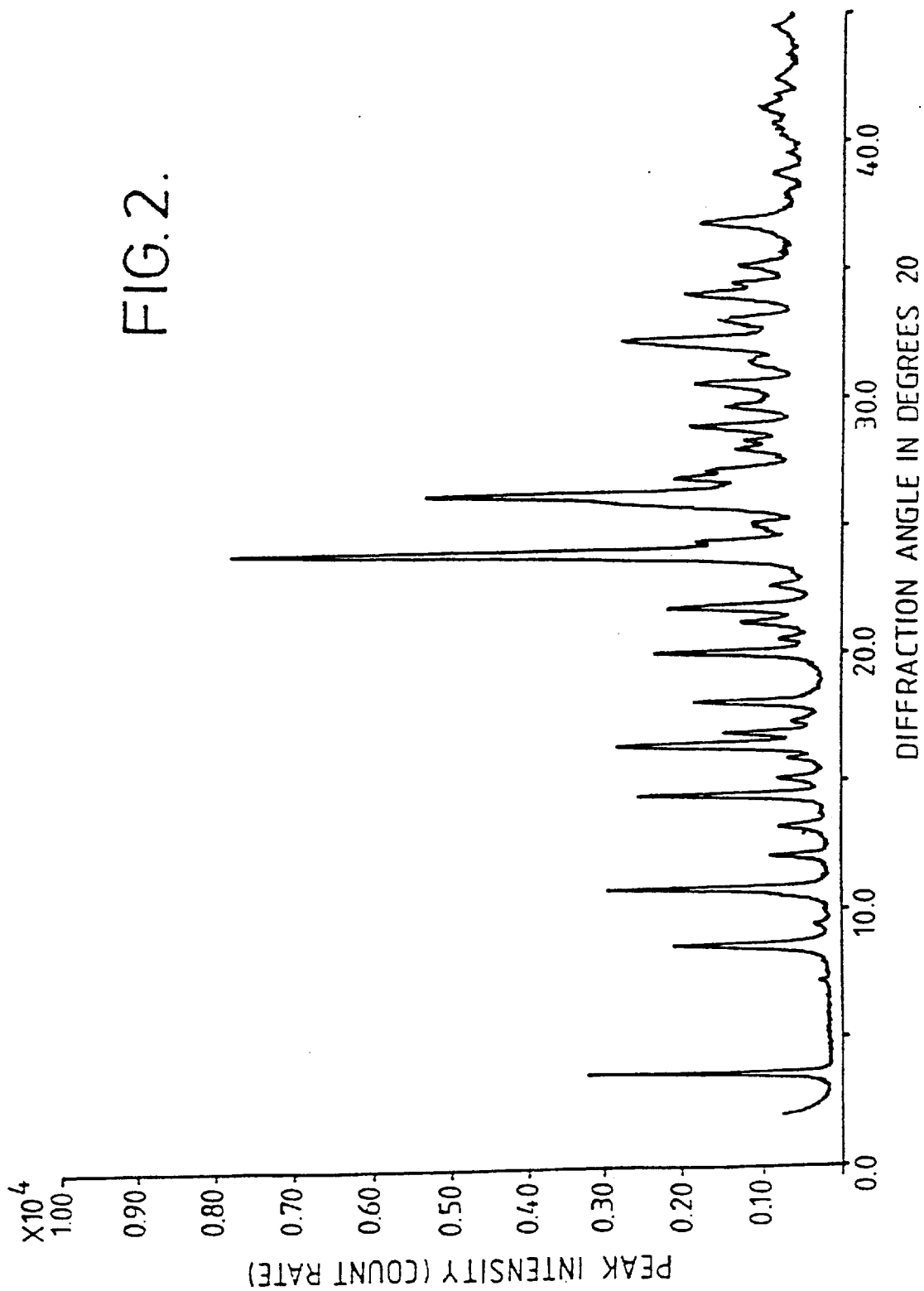

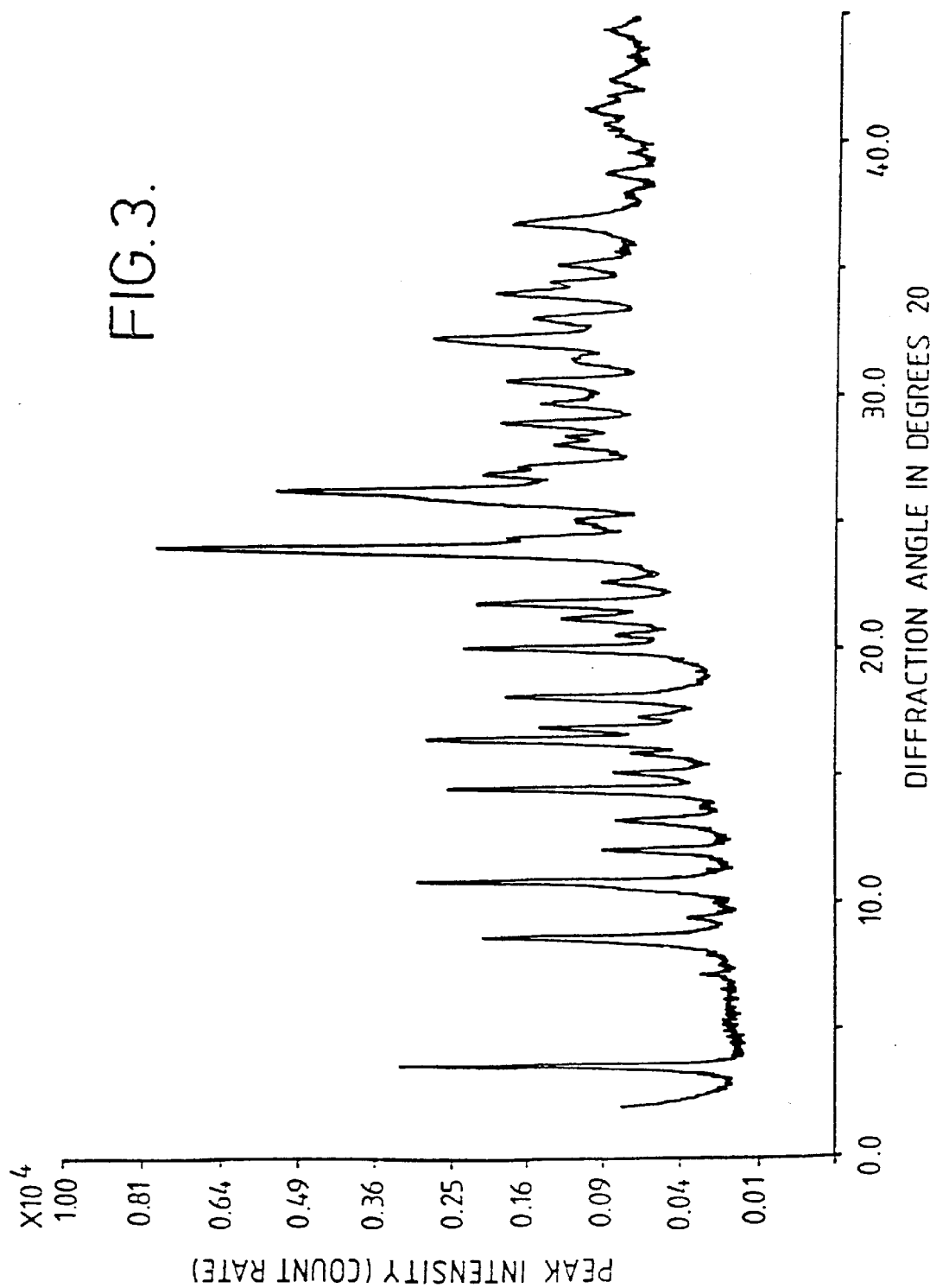

VALACICLOVIR TABLETS CONTAINING COLLOIDAL SILICON DIOXIDE

This application is a 371 of PCT/GB96/00111 filed Jan. 19, 1996.

This invention relates to a tablet of the antiviral drug valaciclovir.

The compound 9-[(2-hydroxyethoxy)methyl]guanine, otherwise known as acyclovir possesses potent antiviral activity and is widely used in the treatment and prophylaxis of viral infections in humans, particularly infections caused by the herpes group in humans (see, for example, Schaeffer et al, Nature, 272, 583–585 (1978), UK Patent No. 1523865, U.S. Pat. No. 4,199,574). However, acyclovir is poorly absorbed from the gastrointestinal tract upon oral administration and this low bioavailability means that multiple high doses or oral drug may need to be administered, especially for the treatment of less sensitive viruses or infections in order to achieve and maintain effective anti-viral levels in the plasma.

The L-valine ester of acyclovir (2-[2-amino-1,6-dihydro-6-oxo-9H-Purin-9yl)methoxy]ethyl L-valinate (herein referred to as valaciclovir) has been shown to possess much improved bioavailability whilst retaining the anti-viral properties of acyclovir. A preferred form of this compound is its hydrochloride salt which is herein referred to as valaciclovir hydrochloride. Valaciclovir and its salts including the hydrochloride salt are disclosed in U.S. Pat. No. 4,957,924 (see particular example 1B), European Patent No. 0308065 (see particularly example IB) and Beauchamp et al, Antiviral Chemistry and Chemotherapy, 3(3), 157–164 (1992) (see particularly page 162 column 1). Tablets of valaciclovir are also generally disclosed in the U.S. Pat. No. 4,957,924 and European Patent No. 0308065.

During development of a tablet formulation containing a high proportion of valaciclovir, we often encountered difficulties in obtaining tablets of sufficient hardness and friability for pharmaceutical handling and for film coating.

If the tablet is too friable, it will chip or break during packaging and transport. The US Pharmacopoeia (USP) no. 23, 1995, p1981 at monograph 1216 requires that pharmaceutical tablets have a friability not exceeding 1%. If the tablet is too soft, it will crumble during, tumbling in the film coating pan.

In the reference manual 'Problem Solver' (compiles by FMC Corporation) at pages 8 and 9, the remedies for low tablet hardness are given inter alia as increasing the compression force applied to form the tablet, or decreasing the proportion of lubricant in the tablet formulation.

We tried to increase the hardness and friability of valaciclovir tablets by increasing the compression force, by decreasing the proportion of lubricant and increasing the proportion of biner, but found in each case that a sufficiently hard and non-friable tablet could not be produced in a practical way.

Furthermore, cracks were found in some tablets as a result of increasing the compression force. Additionally, valaciclovir has 'adhesive' properties in that it can stick to tablet dies and therefore needs to be efficiently lubricated. It is difficult therefore to reduce the proportion of lubricant without causing the tablets to stick. Furthermore, the disintegration time of the valaciclovir tablet is also quite long and therefore any possible solution to the hardness and friability problem should not have a substantial deleterious effect on either the disintegration time or lubrication (as measured by the ejection force) of the table formulation.

It is therefore an object of the invention to provide a robust tablet formulation of valaciclovir and salts thereof which is capable of being film coated and consistently providing tablets having a friability not exceeding 1%, a hardness of at least 9 kP and an ejection force not exceeding 1000 Newtons (1 kN).

The hardness of the tablet should be such that it not only has an acceptable crushing force (as measured by the kP value), but also that the tablet does not break during tumbling.

It is a further preferred object of the invention to provide a robust formulation which is capable of consistently providing tablets substantially free of cracks.

We have now found an effective method of overcoming both of the above friability and hardness problems which involves the extragranular use of colloidal silicon dioxide and microcrystalline cellulose in the tablet formulation.

The Handbook of Pharmaceutical Excipients 1994 at p253–256 does not mention colloidal silicon dioxide as an agent to improve the hardness of tablets. Neither does The Theory and Practice of Industrial Pharmacy (third edition) by Lachman, Lleberman and Kanig, mention colloidal silicon dioxide for such a use.

Accordingly in a first aspect of the invention there is provided a tablet comprising at least about 50% w/w valaciclovir or a salt thereof present within the granules of the tablet, a microcrystalline cellulose filler, a binding agent, a lubricant selected from talc, sodium lauryl sulphate and alkaline earth metal stearates, and about 0.05% to about 3% w/w colloidal silicon dioxide, the lubricant, colloidal silicon dioxide and at least a portion of the filler being present extragranularly, wherein the friability of the tablet does not exceed 1%, the hardness is at least 9 kP and the ejection force does not exceed 1000 Newtons.

A tablet of this formulation containing 0.05% to 3% w/w colloidal silicon dioxide and microcrystalline cellulose is robust, and has a substantially improved friability and hardness. Furthermore such improved properties is achieved while still retaining a satisfactory disintegration time and lubrication properties, even when the formulation is blended under high shear. An excellent tablet providing acyclovir in a highly bioavailable form is thus provided by virtue of the invention.

Preferably the disintegration time of the tablet is not more than about 30 minutes, more preferably not more than about 25 minutes, and most preferably not more than about 20 minutes.

The ejection force should not be more than about 1000 N, preferably not more than about 800 N, more preferably still not more than about 500 N for tablets compressed at about 10 to 30 kN, preferably 10 to 20 kN.

Valaciclovir or a salt thereof are hereinafter referred to generally as the 'active ingredient' or 'drug'.

The 1994 U.S. Pharmacopoeia describes colloidal silicon dioxide (in its monograph) as: a submicroscopic fumed silica prepared by the vapour phase hydrolysis of a silica compound.

Preferably the colloidal silicon dioxide is present in amounts of about 0.05% to about 1% of the total formulation, more preferably at about 0.1% to about 1% w/w, and most preferably about 0.1% to about 0.5% w/w. We have found Aerosil (trade mark) and Cab-o-sil (trade mark) to be very suitable.

BRIEF DESCRIPTION OF THE DRAWINGS

FIGS. 1–3, show X-ray powder diffraction patterns of the product of examples 1B and 2B.

Figure 1:
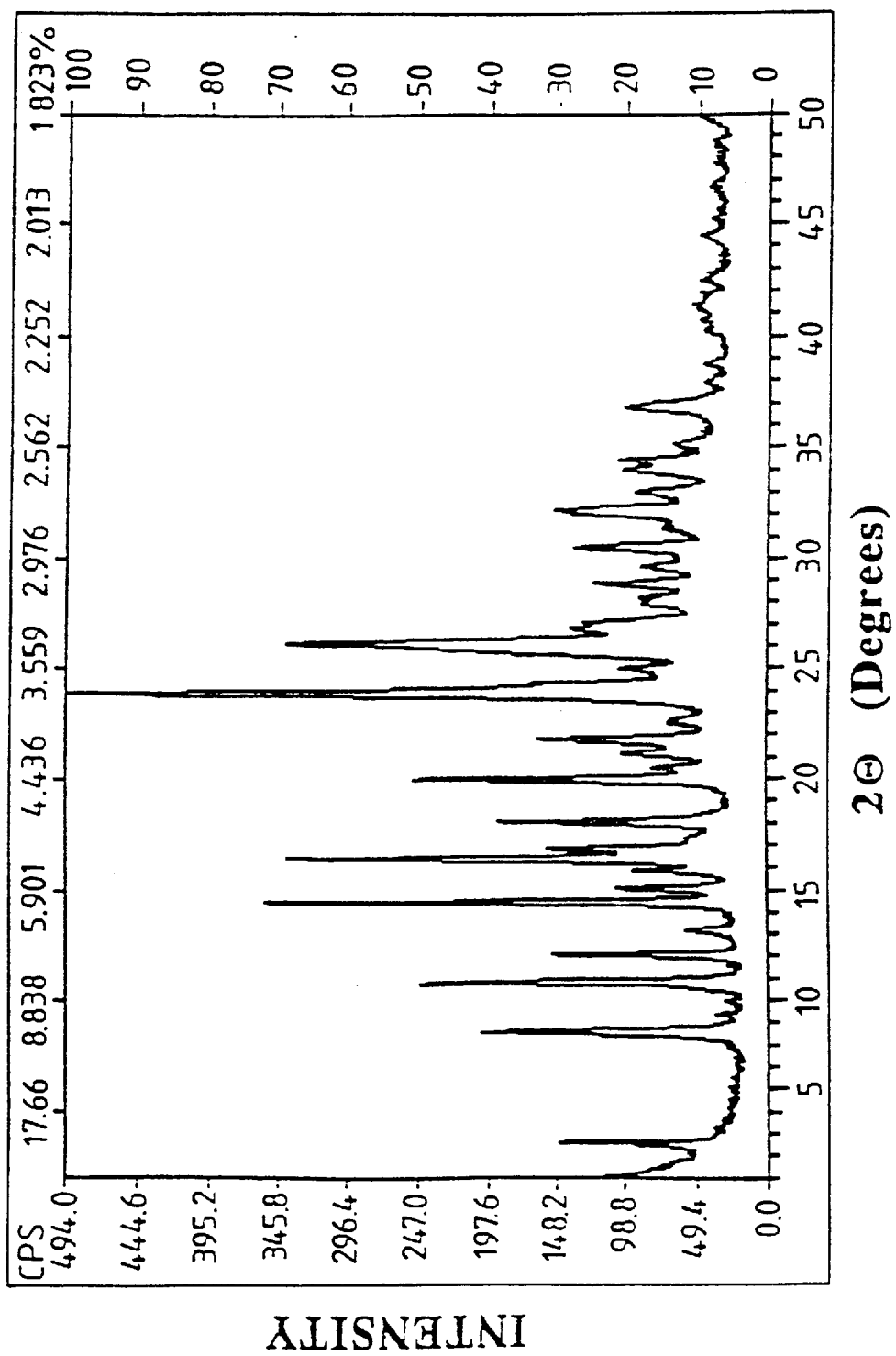

The content of drug in the tablet is at least about 50% w/w, preferably about 60% w/w to about 90% w/w, more preferably still about 65% w/w to about 85% w/w and most preferably about 80% w/w/. Preferably the (tapped) bulk density of the drug is about 0.1 to 0.9 g/cc, more preferably 0.3 to 0.7 g/cc, more preferably still 0.34 to 0.66 g/cc, and most preferably 0.4 to 0.6 g/cc. Suitably the drug is valaciclovir hydrochloride, preferably being of an anhydrous crystalline form including substantially a d-spacing pattern (derived from X-ray powder diffraction) as follows:

d spacing pattern (in Angstroms):

10.20±0.08, 8.10±0.06, 7.27±0.06, 6.08±0.05, 5.83±0.03, 5.37±0.02, 5.23±0.02, 4.89±0.02, 4.42±0.02, 4.06±0.02, 3.71±0.02, 3.39±0.02, 3.32±0.02, 2.91±0.01, 2.77±0.02.

Hereinafter by "anhydrous crystalline form" according to the invention, we mean a crystalline form having substantially the same X-ray powder diffraction pattern as shown in FIGS. 1 to 3, or having substantially the same d pattern a defined above.

Preferably the crystal form purity in any such drug lot of anhydrous crystalline valaciclovir hydrochloride used for valaciclovir tablets is at least 70%, more preferably at least 80%, more preferably still at least 90% and most preferably at least 95% anhydrous crystalline valaciclovir hydrochloride (as characterised above).

In an alternative method for measuring crystal form purity, since the anhydrous crystalline form of valaciclovir hydrochloride contains substantially no water of hydration, the level of other hydrated forms of valaciclovir hydrochloride in any drug lot used for tablets can be measured by the water of hydration content. Preferably any such drug lot of anhydrous crystalline, valaciclovir hydrochloride contain no more than 3% w/w, more preferably no more than 2% w/w, more preferably still not more than 1% w/w and most preferably not more than 0.5% w/w water of hydration.

This water of hydration content is measured by the Keri Fischer method which is well known in the art and is described in the 1990 U.S. Pharmacopoeia at pages 1619–1621, and the European Pharmacopoeia, second edition (1992), part 2, sixteenth fasicule at v. 3.5.6-1.

The filler is microcrystalline cellulose and is at least partly present extragranularly, which mitigates stress cracking of the tablet. A tablet formulation of the invention including colloidal silicon dioxide and extragranular microcrystalline cellulose appears to have a synergistic effect and is particularly good and robust in that tablets of valaciclovir can consistently be made to an acceptable hardness without introducing stress cracks even under a high compression force.

According to a preferred aspect of the invention there is provided a tablet comprising at least 50% w/w valaciclovir or a salt thereof, a binding agent, a lubricant selected from talc, sodium lauryl sulphate and alkaline earth metal stearates, 0.05 to 3% w/w colloidal silicon dioxide, and 3 to 30% of microcrystalline cellulose; wherein the valaciclovir or salt thereof is present within the granules of the tablet, the lubricant, colloidal silicon dioxide, and at least a portion of microcrystalline cellulose is present extragranularly; wherein the friability of the tablet does not exceed 1%, the hardness is at least 9 kP, and the ejection force does not exceed 1000 N.

Preferably the microcrystalline cellulose (e.g. Avicel) present at 5 to 15% w/w, most preferably about 10% w/w. The particle size of the microcrystalline cellulose is preferably 20 to 300µ, more preferably 30 to 200µ, and most preferably 50 to 100µ.

The binding agent serves, for example, to bind the primary and secondary particles together and improve tablet hardness. Preferably the binding agent is present in an amount of about 1% to about 5% w/w, more preferably at about 2% to about 4% w/w, and is suitably a non-starch based binder such as methylcellulose or most preferably povidone. The grade of povidone is advantageously K30 and most preferably K90.

The binding agent such as the povidone, can be dissolved in the granulating solvent (such as water) before adding to the drug, but preferably it is added (at least partly) dry to the drug and other excipients and then the granulating solution (such as povidone in water) added.

The lubricant is suitably present in an amount of about 0.1% to about 2.0% w/w, preferably about 0.1% to about 1.0% w/w. Although talc or sodium lauryl sulphate are suitable, preferably the lubricant is an alkaline earth metal stearate, such as magnesium stearate. The above amounts apply to the stearate, and they are ideally present in amount of at about 0.3% to about 0.6% w/w.

Although valaciclovir is very soluble, especially in its salt form, it is preferable if a disintegrating agent is present in the tablet formulation, suitably in an amount of about 0.5 to about 20% w/w, more preferably at about 0.5% to 7.0% w/w. The disintegrating agent is advantageously present within the granules of the tablet and can be added before or after the binding agent. Clays such as kaolin, bentonite or veegum (trademark), and celluloses such as microcrystalline cellulose or croscarmellose sodium e.g., Ac-Di-Sol (trademark) maybe used as disintegrants. Preferably a non-ionic disintegrant such as crospovidone is used. Preferably, the crospovidone is present at about 0.5% to about 7.0% w/w, more preferably about 2 to about 5% w/w, and preferably a portion is present intragranularly.

A further aspect of the invention provides a process for preparing a tablet comprising at least about 50% w/w valaciclovir or a salt thereof, a binding agent, microcrystalline cellulose filler, a lubricant selected from talc, sodium lauryl sulphate and alkaline earth metal stearates, and about 0.05 to 3.0% w/w colloidal silicon dioxide, wherein the hardness of the tablet is at least 9 kP, the friability is not more than 1%, and the ejection force is not more than 1000 N; said process comprising forming granules which include valaciclovir or a salt thereof and then blending the lubricant, colloidal silicon dioxide and at least a portion of the filler with said granules.

Preferably said process comprises forming granules by mixing said valaciclovir or salt, optionally a binding agent or a portion thereof, and optionally a portion of the filler; granulating with a granulating solution to form granules or dissolving the binding agent or a portion in the granulating solution before adding to valaciclovir; drying the granules; blending the granules with the lubricant, colloidal silicon dioxide, and filler or a portion thereof; and then compressing the blended mixture to form a tablet.

A preferred aspect of the invention provides a process for preparing a tablet comprising at least 50% w/w valaciclovir or a salt thereof, a binding agent, a lubricant selected from talc, sodium lauryl sulphate and alkaline earth metal stearates, 0.05 to 3% w/w colloidal silicon dioxide and 3 to 30% w/w of microcrystalline cellulose filler; wherein the hardness of the tablet is at least 9 kP, the friability is not more than 1%, and the ejection force is not more than 1000 N; said process comprising forming granules by mixing the valaciclovir or salt, optional binding agent or a portion thereof, and optionally a portion of microcrystalline cellulose filler; granulating with a granulating solution to form granules or dissolving the binding agent or a portion thereof in the granulating solution before adding to valaciclovir; drying the granules; blending the granules with the lubricant, colloidal silicon dioxide, and at least a portion of the filler; and then compressing the blended mixture to form a tablet.

the colloidal silicon dioxide can be first blended with the lubricant, preferably a stearate derivative (e.g. magnesium stearate) before blending with the granules or it can be added separately from the lubricant. When the lubricant is a stearate, preferably the ratio or stearate to colloidal silicon dioxide is about 1:1 to 10:1, more preferable about 1:1 to about 3:1.

The present invention also provides a tablet (as described above) for use in medical therapy, e.g. in the treatment of a viral disease in an animal, e.g. a mammal such as a human. The compound is especially useful for the treatment of diseases caused by various DNA viruses, such as herpes infections, for example, herpes simlex 1 and 2, varicella zoster, cytomegalovirus, Epstein-Barr viruses or human herpes virus-6 (HHV-6) as well as diseases caused by hepatitis B. The active compound can also be used for the treatment of papilloma or wart virus infections and, may furthermore be administered in combination with other therapeutic agents, for example with zidovudine, to treat retroviral associated infections in particular HIV infections.

In addition to its use in human medical therapy, the active compound can be administered to other animals for treatment of viral diseases, e.g. to other mammals. The present tablet also provides a method for the treatment of a viral infection, particularly a herpes viral infection, in an animal, e.g. a mammal such as a human, which comprises administering to the host one or more tablets of the invention to provide an effective antiviral amount of the active compound.

The present invention also provides the use of the active compound in the preparation of a tablet of the invention for the treatment of a viral infection.

A tablet of the invention may be administered by any route appropriate to the condition to be treated, but the preferred route of administration is oral. Although tablets generally are included within the scope of the invention, for example a dispersible tablet or chewable tablet, preferably the tablet is a swallowable tablet, most preferably a film-coated swallowable tablet. It will be appreciated however, that the preferred route may vary with, for example, the condition of the recipient.

For each of the above-indicated utilities and indications the amounts required of the active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range 1 to 150 mg per kilogram bodyweight of recipient per day, preferably in the range 5 to 120 mg per kilogram bodyweight per day (Unless otherwise indicated, all weights of the active ingredients are calculated with respect to the free base valaciclovir). The desired dose is preferably presented as one, two, three or four or more sub-doses administered at appropriate intervals throughout the day. These sub-doses may be administered in unit dosage forms, for example, containing about 50 to 2000 mg, preferably about 250, 500, 1000 or 2000 mg of active ingredients per unit dose form.

The following dosage regimes are given for guidance: treatment of herpes simplex virus types 1 and 2 infection:- total daily dose of about 1 or 2 g administered at 500 mg twice a day or 1 g twice a day for 5 to 10 days; suppression of herpes simplex virus types 1 and 2 infections:- total daily dose about 250 mg to 1 g for about one to ten years (depending on the patient);

treatment of varicella zoster virus infections (for example shingles):- daily dose about 3 g administered at 1 g three times a day for seven days; suppression of cytomegalovirus infections:- total daily dose about 8 g administered at 2 g 4 times a day. For transplant patients this daily dose is administered for three to six months for the period at risk; and for HIV positive patients said daily dose is administered as usually indicated for improving quality of life, for example for two years or more.

Early results now indicate that valaciclovir can be used in the effective suppression of recurrent genital herpes at a once daily dose of from about 200 mg to about 1000 mg for an effective treatment period. The most likely daily dosages are 250 mg, 500 mg or 1000 mg.

Valaciclovir hydrochloride was made as described below:

EXAMPLE 1

A. 2-[(2-amino-1,6-dihydro-6-oxo-9H-purine-9-yl) methoxy]ethyl-N-[(benzyloxy)]-L-valinate CBZ-L-value (170 g) was dissolved in dimethylformamide (DMF) (750 ml) and cooled. A cold solution of N,N-dicyclohexyl-carbodiimide (DCC) (156.7 g) in DMF (266 ml) was added and stirred with cooling. Acyclovir (10.1 g) was added in a single portion, and then 4-(dimethylamino) pyridine (9.4 g) was added while maintaining cooling. The mixture was stirred cold overnight. A white precipitate of the by-product was then removed by filtration. The filtrate was reduced in volume by vacuum distillation and the concentrate treated with water (663 ml) then heated to 70° C. The suspension was cooled to 20° C., filtered and the solid washed with water.

The damp, crude material was then purified by recrystallisation from denatured alcohol (1.2 liters) to afford the title compound as a damp white crystalline solid (281.5 g).

B. 2-[(2-amino-1,6-dihydro-6-oxo-9H-purin-9-yl) methoxy] ethyl-L-valinate hydrochloride 2-[(2-amino-1,6-dihydro-6-oxo-9H-purin-9-yl)methoxy] ethyl-N-[(benzyloxy)carbonyl]-L-valinate (175 g) was charged to aqueous denatured alcohol (335 ml/795 ml) and heated to reflux. The solution was then cooled to 40° C. The suspension was treated with 5% palladium on carbon catalyst (35 g wet weight 50% wet with water) then formic acid (30.6 ml of 90% w/w) added over 1 hour. The reaction mixture was stirred for a further 1 hour then a second charge of formic acid made (19.5 ml) and the mixture filtered to remove the catalyst. The filter cake was washed with denatured alcohol and the combined filtrates were treated with concentrated hydrochlorid acid (33.7 ml) and the resultant mixture was concentrated by vacuum distillation.

Acetone (1295 ml) was then added over 15 minutes and the suspension stirred for 1 hour before filtering off the product. The solid was then slurried with acetone (circa. 530 ml), refiltered and dried at 60° C. in vacuo to give the title compound (1123 g:81.6%).

A 15 g sample of this material was combined with denatured alcohol (circa. 7 ml), to moisten and was heated with agitation at 60° C. overnight in a closed flask to avoid loss of alcohol and maintain the dampness of the mixture. The mixture was then dried at 60° C. in vacuo to afford the product as the desired morphic form.

Physical Data:

Karl Fischer value: 0.9% w/w water.

The X-ray powder diffraction patterns of the product of example 1B are shown in FIG. 1 of the accompanying drawings.

The d spacings and further X-ray diffraction data are shown in Table 1.

TABLE 1

| Peak No: | Angle (degrees) | Peak (counts) | d Spacing pattern (Å) | Error in d (± Å) | I/Imax (%) |
|---|---|---|---|---|---|
| 1 | 3.56 | 680 | 24.8 | 0.5 | 24 |
| 2 | 8.62 | 1151 | 10.25 | 0.08 | 39 |
| 3 | 9.42 | 87 | 9.38 | 0.07 | 3 |
| 4 | 10.86 | 1438 | 8.14 | 0.06 | 49 |
| 5 | 12.10 | 835 | 7.31 | 0.06 | 28 |
| 6 | 13.22 | 198 | 6.69 | 0.05 | 6 |
| 7 | 14.49 | 2172 | 6.11 | 0.05 | 75 |
| 8 | 15.12 | 455 | 5.85 | 0.03 | 15 |
| 9 | 15.90 | 352 | 5.57 | 0.02 | 12 |
| 10 | 16.45 | 1969 | 5.38 | 0.02 | 68 |
| 11 | 16.90 | 744 | 5.24 | 0.02 | 25 |
| 12 | 17.33 | 119 | 5.11 | 0.02 | 4 |
| 13 | 18.12 | 1013 | 4.89 | 0.02 | 35 |
| 14 | 22.71 | 1429 | 4.43 | 0.02 | 49 |
| 15 | 20.55 | 256 | 4.32 | 0.02 | 8 |
| 16 | 21.21 | 370 | 4.19 | 0.02 | 12 |
| 17 | 21.83 | 753 | 4.07 | 0.02 | 26 |
| 18 | 22.71 | 95 | 3.91 | 0.02 | 3 |
| 19 | 23.95 | 2893 | 3.71 | 0.02 | 100 |
| 20 | 25.10 | 171 | 3.54 | 0.02 | 5 |
| 21 | 26.21 | 1784 | 3.40 | 0.02 | 61 |
| 22 | 26.89 | 428 | 3.31 | 0.02 | 14 |
| 23 | 27.08 | 373 | 3.29 | 0.02 | 12 |
| 24 | 28.02 | 158 | 3.18 | 0.02 | 5 |
| 25 | 28.27 | 161 | 3.15 | 0.02 | 5 |
| 26 | 28.91 | 391 | 3.09 | 0.02 | 13 |
| 27 | 29.68 | 191 | 3.01 | 0.02 | 6 |
| 28 | 30.55 | 502 | 2.92 | 0.02 | 17 |
| 29 | 31.34 | 110 | 2.85 | 0.02 | 3 |
| 30 | 31.58 | 98 | 2.83 | 0.02 | 3 |
| 31 | 32.13 | 597 | 2.78 | 0.02 | 20 |
| 32 | 32.96 | 260 | 2.72 | 0.02 | 8 |
| 33 | 33.99 | 344 | 2.64 | 0.02 | 11 |
| 34 | 34.38 | 374 | 2.61 | 0.02 | 12 |
| 35 | 35.12 | 141 | 2.55 | 0.02 | 4 |
| 36 | 36.78 | 408 | 2.44 | 0.02 | 14 |
| 37 | 38.71 | 101 | 2.32 | 0.02 | 3 |

I/Imax = (peak height/max. peak ht) × 100

The powder sample used to produce the above X-ray diffraction data was prepared by an equivalent method as the powder sample used to produce the X-ray diffraction data of table 2 (described hereinafter) except that for the above data the following preparation was used to prepare the powder sample.

The sample was prepared by milling 1 g of sample in a plastic cup using two acrylic balls for 5 minutes with a Chemplex Spectromill. The samples were then back packed against a glass slide to a depth of 2 mm.

The X-ray diffraction scan was obtained using a Scintag PADV diffractometer in the step scan mode at 0.02° per step and a 10 second count per step. The sample holder was spun at 1 rotation per second during the scan. Additional setting as described below.
X-ray generator: 45 kV, 40 mA
Radiation: Copper K alpha radiation
Fixed divergent slit: 1 mm
Incident scatter slit: 2 mm
Diffracted scatter slit: 0.5 mm
Receiving slit: 0.3 mm
Goniometer radius: 235 mm
Detector: Scintillation with a graphite monochromator.

The peak intensities are reported as absolute counts of the peak top. The intensity units on the X-ray diffraction plot are counts/sec. The absolute counts=counts/sec×count time= counts/sec×10 sec. The peak intensities in the table have been corrected for background and copper K alpha II X-ray wavelength contribution.

EXAMPLE 2
A. 2-[(2-amino-1,6-dihydro-6-oxo-9H-purin-9-yl) methoxylethyl-N-[(benzyloxy)carbonyl]-L-valinate CBZ-L-valine (167 g) was dissolved in dimethylformamide (DMF) (750 ml) and cooled to 0.5° C. A cold solution of N,N-dicyclohexylcarbodiimide (DCC) (153.5 g) in DMF (266 ml) was added followed by acyclovir (111.7 g) in a single portion. 4(Dimethylamino)pyridine (9.4 g) was then added and the mixture stirred cold overnight. A white precipitate of the by-product was then removed by filtration. The solvent was partially removed by vacuum distillation and the concentrate treated with water (663 ml) then heated to 70° C. The suspension was cooled to 20° C., filtered and the solid washed with water.

The damp, crude material was then purified by recrystallisation from denatured alcohol (1.2 liters) to afford the title compound as a damp white crystalline solid (215.3 g).

B. 2-[(2-amino-1,6-dihydro-6-oxo-9H-purin-9-yl) methoxylethyl-N-L-valinate hydrochloride 2-[(2-amino-1,6-dihydro-6-oxo-9H-purin-9-yl)methoxy] ethyl-N-[(benzyloxy)carbonyl]-L-valinate (200 g) was charged to aqueous denatured alcohol (382 ml/908 ml) and heated to reflux to dissolve solids. The solution was cooled to 40° C. The suspension was treated with a 50% w/w paste of 5% palladium on carbon catalyst and water (40 g) then formic acid (96% w/w:32.8 ml) added over 1 hour. The reaction mixture was stirred for a further 1 hour then a second charge of formic acid made (20.88 ml) and the mixture filtered to remove the catalyst. The filtrate was treated with concentrated hydrochloric acid (38.56 ml) and the resultant mixture was concentrated under vacuum.

Acetone (1480 ml) was then added over 15 minutes and the suspension stirred for 1 hour before filtering off the product. The solid was then slurried with acetone (ca. 500 ml), refiltered and dried at 60° C. in vacuo to give the title compound (137.75 g:87.6%).

A 10 g sample of this material was combined with denatured alcohol (3.5 ml), heated at 60° C. for several hours and the solvent then removed in vacuo to afford the product as the desired morphic form.

Crystal From Purity: the sample of example 2(B) contained above 90% of the anhydrous crystalline form valaciclovir.

The X-ray powder diffraction patterns of the product of example 2(B) are shown in FIGS. 2 and 3 of the accompanying drawings in which:

FIG. 2 is a linear plot X-ray diffractogram; and
FIG. 3 is a square root plot X-ray diffractogram.

The d spacings and further X-ray diffraction data are shown in Table 2.

TABLE 2

| Peak No: | Angle (degrees) | Peak (counts) | d Spacing pattern (Å) | I/Imax (%) |
|---|---|---|---|---|
| 1 | 3.62 | 2673 | 24.40 | 35 |
| 2 | 7.21 | 119 | 12.26 | 2 |
| 3 | 8.64 | 1910 | 10.22 | 25 |
| 4 | 9.43 | 180 | 9.37 | 2 |
| 5 | 10.86 | 2652 | 8.14 | 35 |
| 6 | 12.12 | 734 | 7.30 | 10 |
| 7 | 13.24 | 615 | 6.68 | 8 |
| 8 | 13.77 | 106 | 6.42 | 1 |
| 9 | 14.50 | 2333 | 6.11 | 31 |
| 10 | 15.14 | 635 | 5.85 | 8 |
| 11 | 15.89 | 511 | 5.57 | 7 |
| 12 | 16.44 | 2652 | 5.39 | 35 |

TABLE 2-continued

| Peak No: | Angle (degrees) | Peak (counts) | d Spacing pattern (Å) | I/Imax (%) |
|---|---|---|---|---|
| 13 | 16.90 | 1267 | 5.24 | 17 |
| 14 | 17.33 | 475 | 5.11 | 6 |
| 15 | 18.13 | 1648 | 4.89 | 22 |
| 16 | 20.05 | 2172 | 4.43 | 28 |
| 17 | 20.56 | 640 | 4.32 | 8 |
| 18 | 21.20 | 1096 | 4.19 | 14 |
| 19 | 21.78 | 2034 | 4.08 | 27 |
| 20 | 21.90 | 1384 | 4.06 | 18 |
| 21 | 22.66 | 729 | 3.92 | 10 |
| 22 | 23.94 | 7621 | 3.71 | 100 |
| 23 | 24.39 | 1624 | 3.65 | 21 |
| 24 | 25.11 | 967 | 3.54 | 13 |
| 25 | 25.86 | 2460 | 3.44 | 32 |
| 26 | 26.21 | 5127 | 3.40 | 67 |
| 27 | 26.82 | 1892 | 3.32 | 25 |
| 28 | 26.89 | 1927 | 3.31 | 25 |
| 29 | 27.19 | 1429 | 3.28 | 19 |
| 30 | 27.99 | 1156 | 3.18 | 15 |
| 31 | 28.35 | 1076 | 3.15 | 14 |
| 32 | 28.87 | 1722 | 3.09 | 23 |
| 33 | 28.94 | 1529 | 3.08 | 20 |
| 34 | 29.62 | 1274 | 3.01 | 17 |
| 35 | 30.56 | 1673 | 2.92 | 22 |
| 36 | 31.30 | 999 | 2.86 | 13 |
| 37 | 32.25 | 2570 | 2.77 | 34 |
| 38 | 33.04 | 1376 | 2.71 | 18 |
| 39 | 34.00 | 1806 | 2.63 | 24 |
| 40 | 34.45 | 1225 | 2.60 | 16 |
| 41 | 35.13 | 1149 | 2.55 | 15 |
| 42 | 36.77 | 1600 | 2.44 | 21 |
| 43 | 38.01 | 576 | 2.37 | 8 |
| 44 | 38.76 | 729 | 2.32 | 10 |
| 45 | 39.52 | 524 | 2.28 | 7 |
| 46 | 40.70 | 751 | 2.22 | 10 |
| 47 | 41.28 | 870 | 2.19 | 11 |
| 48 | 41.88 | 686 | 2.16 | 9 |
| 49 | 42.47 | 718 | 2.13 | 9 |
| 50 | 43.40 | 548 | 2.08 | 7 |
| 51 | 44.53 | 729 | 2.03 | 10 |

The diffraction patterns of the product of example 2B were generated on a Phillips PW1800 Automatic X-ray Powder Diffractometer using a scan of 2 to 45 2$\Theta$ with step intervals of 0.02 degrees and an integration time of 4 seconds per step.

Generator settings: 40 KV, 45 mA, Cu alpha 1,2 wavelengths: 1.54060, 1.54439 Å; Step size, sample time: 0.020 deg, 4.00 s, 0,005 deg/s; monochromator used: yes; divergence slit: automatic (irradiated sample length: 10.0 mm); peak angle range: 2.000–45.000 deg; range in D spacing: 44.1372–2.01289 Å; peak position criterion: top of smoothed data; cryst peak width range: 0.00–2.00 deg; minimum peak significance: 0.75 maximum intensity: 7621 cts, 1905.3 cps.

The powder sample was prepared as follows:

A 1 gram portion of valaciclovir hydrochloride was transferred to a Retsch 10 ml polystyrol container ref 31-762 containing 2 acrylic balls ref 26-253 and was then ground to a very fine powder using a Retsch MM2 miser mill set at 100% power for five minutes. The ground powder was back loaded into a Philips PW1811/10 sample holder which had been placed inverted on a perfectly smooth surface (e.g. that afforded by a glass plate or a highly polished metal sheet). The powder was then packed into the holder and further powder added and packed until the holder was full. A Philips PW 1811 00 bottom plate was then clamped into the holder and the entire assembly was then inverted before removing the glass/metal plate in an upwards direction to reveal the smooth sample surface which was flush with that of the holder.

The invention is illustrated below in the following examples and the properties of the tablets show in table 3 hereafter.

| | | | | | | | | | | | | | | | |
|---|---|---|---|---|---|---|---|---|---|---|---|---|---|---|---|
| | Example | | | | | | | | | | | | | | |
| | 3 | | | 4 | | | 5 | | | 6 | | | 7 | | |
| Ingredients | mg/ tablet | kg/ Batch | w/w | mg/ tablet | kg/ Batch | w/w | mg/ tablet | kg/ Batch | w/w | mg/ tablet | kg/ Batch | w/w | mg/ tablet | kg/ Batch | w/w |
| Core[1] (intra granular): | | | | | | | | | | | | | | | |
| valaciclovir hydrochloride*[2] | 576.5 | 0.9916 | 82.0 | 576.5 | 0.9916 | 82.8 | 576.5 | 0.9916 | 82.3 | 576.5 | 0.9973 | 82.3 | 576.5 | 0.9973 | 82.0 |
| microcrystalline cellulose (Avicel PH101) | 70.0 | 0.1204 | 10.1 | 70.0 | 0.1204 | 10.0 | 70.0 | 0.1204 | 10.0 | — | — | — | — | — | — |
| crossprodione povidone K30 | 28.0 | 0.04816 | 4.0 | 28.0 | 0.04816 | 4.0 | 28.0 | 0.04816 | 4.0 | 14.0 | 0.02422 | 2.0 | 14.0 | 0.02422 | 2.0 |
| povidone K90 extragranular: | 22.0 | 0.03784 | 3.1 | 22.0 | 0.03784 | 3.2 | 22.0 | 0.03784 | 3.1 | 22.0 | 0.03806 | 3.1 | 22.0 | 0.03806 | 3.1 |
| micro[3] crystalline cellulose (Avicel PH101) | — | — | — | — | — | — | — | — | — | 70.0 | 0.05600 | 10.0 | 70.0 | 0.05600 | 10.0 |
| crospovidone | — | — | — | — | — | — | — | — | — | 14.0 | 0.11200 | 2.0 | 14.0 | 0.01120 | 2.0 |
| collodial silicon dioxide (CAB-O-SIL M-5 ®) | 2.0 | 0.00160 | 0.3 | — | — | — | — | — | — | — | — | — | 2.0 | 0.00160 | 0.3 |

-continued

| | | | | | | | | | | | | | | | |
|---|---|---|---|---|---|---|---|---|---|---|---|---|---|---|---|
| magnesium sterate | 4.0 | 0.0032 | 0.6 | 4.0 | 0.0032 | 0.6 | 4.0 | 0.00320 | 0.6 | 4.0 | 0.00320 | 0.6 | 4.0 | 0.00320 | 0.6 |
| TOTAL WEIGHT | 702.5 | 1.2028 | 100.0 | 696.5 | 1.198 | 100.0 | 700.5 | 1.2012 | 100.0 | 700.5 | 1.12998 | 100.0 | 702.5 | 1.13158 | 100.0 |

*Bulk density 0.6 g/cc after 50 taps (anhydrous crystalline form): Karl Fischer water content = 0.4.
[1]Core weight per batch: 0.5572 kg for examples 3, 4 and 5; 0.4900 kg for examples 6 and 7.
[2]Factor 1.153 = 100
[3]Average particle size about 50μ

| | Example | | | |
|---|---|---|---|---|
| | 8 | | 9 | |
| Ingredients | mg/table | w/w | mg/table | w/w |
| valaciclovir hydrochloride* | 615 | 65.80 | 615 | 65.74 |
| lactose | 205 | 21.93 | 205 | 21.91 |
| microcrystalline[1] cellulose (Avicel PH101) (intragranular) | 75 | 8.02 | 75 | 8.02 |
| povidone K30 | 18 | 19.3 | 18 | 1.92 |
| crospovidone (intragranular) | 18 | 1.93 | 18 | 1.92 |
| colloidal silicon dioxide (Aerosil 200) | 0.0 | 0.0 | 0.9 | 0.10 |
| magnesium stearate | 3.6 | 0.39 | 3.6 | 0.38 |
| TOTAL WEIGHT | 934.6 | 100.0 | 935.5 | 100 |

*bulk density 0.45 g/cc after 50 taps (anhydrous crystalline form)
[1]Average particle size about 50μ.

| | Example | | | |
|---|---|---|---|---|
| | 10 | | 11 | |
| Ingredients | mg/table | w/w | mg/table | w/w |
| valaciclovir hydrochloride* | 580 | 81.01 | 580 | 82.60 |
| lactose | — | — | — | — |
| microcrystalline cellulose[2] (Avicel PH101) (intragranular) | 70 | 9.78 | — | — |
| microcrystalline cellulose (extrangranular) | — | — | 70.4 | 10.03 |
| povidone K30 | 35 | 4.89 | — | — |
| povidone K90 | — | — | 21.7 | 3.09 |
| crosrovidone (intragranular) | 28 | 3.91 | 12 | 1.71 |
| crospovidone (extragranular) | — | — | 14.1 | 2.01 |
| magnesium stearate | 3.0 | 0.42 | 4.0 | 0.57 |
| TOTAL WEIGHT | 716 | 100.0 | 702.2 | 100.0 |

*bulk density 0.38 g/cc after 50 taps (anhydrous crystalline form)
[2]Average particle size about 50μ.

The tables of the examples were made as disclosed below.

EXAMPLES 3 TO 7

Step 1. The core ingredients were sifted with a 20 mesh hand screen, and then blended in an appropriately sized V-shell blender for 10 minutes.

Step 2. The blended powders from Step 1 were then granulated in a 10 liter high shear mixer (model-SP1) by adding pure water while mixing. Approximately 11–14% water, w/w of the core ingredients was then added and the mixture massed for 3 to 4½ minutes.

Step 3. The granule from Step 2 was dried in a tray (examples 5, 6 and 7) or vacuum (examples 3 and 4) drier (model-SP1) at a temperature of 50° C. to an acceptable moisture content of approximately 1.0 to 2.0% L.O.D.

Step 4. The remaining ingredients were sifted through a 20 mesh screen and added to the core ingredients of step 3, and then the mixture was sifted using a Comil Model 197 AS fitted with a 0.062" screen.

Step 5. The mixture was then blended in an appropriately sized V-shell blender for 5 minutes.

Step 6. The blended granule from Step 5 was compressed on a Manesty Beta Press fitted with capsule shaped tooling, 18.25 mm×7.14 mm, at a compression weight of approximately 700 mg and a compression force of about 14.5 to 18 kN.

Step 7. The tablet can then optionally be film coated by using standard methods such as using white colour concentrate, methylhydroxypropylcellulose titanium dioxide, polyethylene glycol and polysorbate.

Hardness (crushing force through the long axis) was measured using a Key hardness tester, Model HT-300 Friability (percent weight loss after 100, six inch drops) was measured in accordance with the USP no. 23, 1995, p1981 at monograph 1216, using an Erweke friability tester, Model TA-3. Physical properties were measured at comparable compression forces. The disintegration time was measured in accordance with the monograph in USP 23 (1995) at page 1790.

EXAMPLES 8 AND 9

Step 1. The following ingredients as shown were sifted with a hand screen.

30 Mesh valaciclovir hydrochloride 5.289 kg
lactose 1.763 kg
microcrystalline Cellulose 0.6450 kg
povidone K30 0.1548 kg
crospovidone 0.1548 kg 60 Mesh magnesium stearate 0.03096 kg colloidal silicon dioxide (CSD) 0.002598 kg Step 2. The 30 mesh sifted ingredients from Step 1 were then blended, excluding the povidone, in a 1 cubic foot V-shell blender for 10 minutes.

Step 3. 1.540 kg of SD3A alcohol (ethanol denatured with 5% methanol) was then mixed with 0.6600 kg of purified water and the screened povidone, 0.1548 kg, was dissolved in 0.6192 kg of the mixed solvents by hand stirring.

Step 4. The blended powders from Step 2 were than granulated in a 1 cubic foot Littleford Lodige mixer by adding the dissolved povidone while mixing. 1.315 kg of more mixed solvent was added and the mixture massed for seven minutes total as shown below.

Ploughs 7 min
Choppers 6.5 min

Step 5. The granule from Step 4 was then dried in a Fluid Bed Dryer (Glatt GPCG5) with an inlet air temperature of 50° C. to any acceptable moisture content of approximately 1.0 to 3.0% L.O.D.

Step 6. The granule from Step 5 was then sifted using a Fitz Mill Model M fitted with a 30 mesh screens, with knives forward, operating at medium speed.

Step 7. The screened magnesium stearate from step 1 was added to the granule from Step 6 and blended for 5 minutes using the blender from Step 2. This was labelled as example 10 (2.650 kg).

Step 8. Part of the blended granule from Step 7 was compressed on a Manesty Beta Press fitted with oval tooling, 19.1 mm×10.2 mm, at a compression weight of approximately 934.6 mg.

Step 9. The remainder of the lubricated granule 2.650 kg (from Step 7) was weighed and the sifted CSD from step 1 added, then dispersed by hand and the mixture blended for 5 minutes in the blender from Step 3. This portion was labelled as Example 11. The mixture was compressed to form tablets.

Examples 10 and 11 were manufactured in a substantially similar manner to Examples 9 and 10 with the following exceptions.

1. All ingredients were sifted through a 20 mesh sieve.
2. Drug and intragranular ingredients were blended for 10 minutes.
3. The amounts of water and SD3A alcohol were adjusted for the difference in batch size.
4. Dried granule was milled using a Comil Model 197AS with 0.062" screen.
5. Example 11 was dried in a tray drier.
6. The magnesium stearate was blended for 10 minutes after 10 minutes preblend of the milled granule and other ingredients.

TABLE 3

| Example Numbers | Compression Force (kN) | Hardness (kP) | Friability (%) | Disintegration Time (mins) | Ejection Force (Newtons) | Stress Cracks (after heating[1]) |
|---|---|---|---|---|---|---|
| 3a) | 15.256 | 10.0 | 0.035 | 15.36 | 395 | Yes |
| 3b) | 17.896 | 13.3 | 0.041 | 16.60 | 452 | Yes |
| 4 | 14.716 | 8.2[3] | 0.107 | 13.94 | 305 | Yes[2] |
| 5a) | 15.343 | 9.9 | 0.15 | 17.95 | 300 | Yes |
| 5b) | 17.956 | 12.5 | 0.10 | 19.96 | 329 | Yes |
| 6a) | 15.058 | 11.9 | 0.15 | 18.04 | 306 | Yes/faint |
| 6b) | 17.771 | 14.7 | 0.14 | 17.68 | 324 | Yes |
| 7a) | 15.495 | 12.6 | 0.13 | 18.89 | 366 | No |
| 7b) | 17.896 | 15.3 | 0.14 | 20.11 | 411 | No |
| 8a) | 14.3 | 5.9 | 1.78 | not available (N/A) | 410 | |
| 8b) | 31.4 | 9.7 | 1.70 | N/A | 450 | |
| 9a) | 14.7 | 13.6 | 0.04 | 10.3 | 332 | |
| 9b) | 30.7 | 22.8 | 0.03 | 12.6 | 330 | |
| 10 | Setting 6 | 14.4 | | N/A | N/A | Yes |
| 11 | Setting 7 | 15.5 | | N/A | N/A | No |

[1]Heated in a 50° C. forced air oven to simulate film coating.
[2]Stress cracks before and after heating.
[3]One tablet broke in half (unacceptable hardness)

As can be seen from the results, the tablet of example 4 (which lacks colloidal silicon dioxide and has microcrystalline cellulose intragranularly broke in half during tumbling, to simulate film coating conditions. The hardness of the tablet is therefore totally unacceptable. On the contrary, when colloidal silicon dioxide was added (example 3) the tablet surprisingly did not break and furthermore the disintegration time and ejection force increased by substantially less than would be expected.

The tablets of examples 5 and 6, like that of example 3, developed stress cracks after heating. In the tablet of example 3 there was present colloidal silicon dioxide and intragranular microcrystalline cellulose; in example 5 the microcrystalline cellulose was also intragranular, but there was no colloidal silicon dioxide; and in example 6 again there was no colloidal silicon dioxide, but the microcrystalline cellulose was extragranular. Surprisingly, however, when colloidal silicon dioxide is present and the microcrystalline cellulose is extragranular, there appears to be synergy which prevents stress cracking. This effect can be seen in the tablet of example 7 where there are no stress cracks, and furthermore the hardness and friability were good. As with the tablet of example 3, the disintegration and ejection force were increased substantially less than would be expected.

As can also be seen from comparative example 8a) the hardness value is very low and the friability fails the US Pharmacopoeia (USP) limit of 1%. Even at the very high compression force used in example 8b), the friability still fails the USP test.

In contrast on the addition of about 0.1% w/w of colloidal silicon dioxide (in example 9a and b), hardness and friability have dramatically improved. Furthermore the ejection force, which was good before the addition of colloidal silicon dioxide is still good, and in face actually improved on its addition. The disintegration time of the tablets of example 9 is also very satisfactory.

Additionally when the formulation of example 11 is repeated incorporating colloidal silicon dioxide in amounts ranging from 0.05 to 3% w/w, excellent tablets can be consistently produced having a high hardness and low friability value, substantially free of stress-cracks.

The robust tablet formulation of the invention therefore can consistently provide valaciclovir tablets having excellent handling characteristics which are suitable for film coating and which still have an adequate lubricating and disintegration time.

We claim:

1. A tablet comprising at least about 50% w/w valaciclovir or a salt thereof, a microcrystalline cellulose filler, a binding agent, a lubricant selected from the group consisting of talc, sodium lauryl sulphate and alkaline earth metal stearates and about 0.05 to about 3% w/w colloidal silicon dioxide wherein the valaciclovir or a salt thereof is present within the granules of the tablet, the lubricant, silicon dioxide and at least a portion of the filler is present extragranularly; wherein the friability of the tablet does not exceed 1%, the hardness is at least 9 kP, and the ejection force does not exceed 1000 Newtons.

2. A tablet as claimed in claim 1 wherein the colloidal silicon dioxide is present in an amount of about 0.1% to about 0.5% w/w.

3. A tablet as claimed in claim 1 wherein the filler is present in an amount of about 3% w/w to about 30% w/w.

4. A tablet as claimed in claim 3 wherein the filler is present at about 5% to about 15% w/w.

5. A tablet as claimed in claim 4, wherein the filler is present at about 10% w/w.

6. A process for preparing a tablet comprising at least about 50% w/w valaciclovir or a salt thereof, a binding agent, a lubricant selected from the group consisting of talc, sodium lauryl sulphate and alkaline earth metal stearate, about 0.05 to about 3% w/w colloidal silicon dioxide, and about 3 to about 30% w/w or microcrystalline cellulose filler; wherein the hardness of the tablet is at least 9 kPk, the friability is not more than 1%, and the ejection force is not more than 1000 N; said process comprising forming granules by mixing the valaciclovir or salt, optional binding agent or a portion thereof, and optionally a portion of filler; granulating with a granulating solution to form granules or dissolving the binding agent or a portion thereof in the granulating solution before adding to valaciclovir; drying the granules; blending the granules with the lubricant, colloidal silicon dioxide, and at least a portion of the filler; and then compressing the blended mixture to form a tablet.

7. A tablet as claimed in claim 1, wherein the particle size of filler is about 20 to about 300 $\mu$m.

8. A tablet as claimed in claim 1 wherein the binding agent is present at about 1% to about 5% w/w.

9. A tablet as claimed in claim 1 wherein the binding agent is methylcellulose or povidone.

10. A tablet as claimed in claim 9 wherein the binding agent is povidone.

11. A tablet as claimed in claim 10 wherein the povidone is povidone K90 grade.

12. A tablet as claimed in claim 1 wherein the lubricant is present at about 0.1% to about 2.0% w/w.

13. A tablet as claimed in claim 12 wherein the lubricant is an alkaline earth metal stearate.

14. A tablet as claimed in claim 13 wherein the lubricant is magnesium stearate and is present at about 0.1% to about 1.0% w/w.

15. A tablet as claimed in claim 1 wherein the valaciclovir or its salt is present at about 65% to about 85% w/w.

16. A tablet as claimed in claim 1 comprising valaciclovir hydrochloride.

17. A tablet as claimed in claim 16 wherein the valaciclovir hydrochloride is anhydrous crystalline form including substantially a d spacing pattern as follows:

d spacing pattern (in Angstroms):

10.20±0.08, 8.10±0.06, 7.27±0.06, 6.08±0.05, 5.83±0.03, 5.37±0.02, 5.23±0.02, 4.89±0.02, 4.42±0.02, 4.06±0.02, 3.71±0.02, 3.39±0.02, 3.32±0.02, 2.91±0.02, 2.77±0.02.

18. A tablet as claimed in claim 1 wherein the tapped bulk density of valaciclovir or salt thereof is about 0.1 to about 0.9 g/cc.

19. A tablet as claimed in claim 1 which further includes a disintegrating agent present at about 0.05% to about 20% w/w.

20. A tablet as claimed in claim 19 wherein the disintegrating agent is a non-ionic disintegrating agent.

21. A tablet as claimed in claim 20 wherein the disintegrating agent is crospovidone present at about 0.5% to about 7% w/w.

22. A tablet comprising about 65% to about 85% w/w anhydrous crystalline valaciclovir hydrochloride including the d spacing diffraction pattern of claim 17, about 0.5% to about 5% w/w of povidone, about 3% to about 30% w/w of a microcrystalline cellulose filler, about 0.5 to about 7% w/w of a non-ionic disintegrating agent, about 0.1% to about 1.0% of an alkaline earth metal stearate lubricant and about 0.1% to about 0.5% w/w of colloidal silicon dioxide, wherein the valaciclovir hydrochloride is present intragranularly; and wherein the filler, stearate lubricant and colloidal silicon dioxide are present extragranularly.

23. A tablet as claimed in claim 1 which is film coated.

24. A tablet as claimed in claim 1 for use in medical therapy.

25. A method of treatment of a herpes virus infection in a human comprising administering to the host one or more tablets as claimed in claim 1 to administer an effective anti-herpes viral amount of valaciclovir or a salt thereof.

26. A process for preparing a tablet comprising at least about 50% w/w valaciclovir or a salt thereof, a binding agent, a microcrystalline cellulose filler, a lubricant selected from the group consisting of talc, sodium lauryl sulphate and alkaline earth metal stearate and about 0.05 to about 3.0% colloidal silicon dioxide, wherein the friability of the tablet does not exceed 1%, the hardness is at least 9 kP and the ejection force does not exceed 10000 N; said process having the valaciclovir or its salt present within the granules of the tablet, and the lubricant, colloidal silicon dioxide, and at least a portion of the microcrystalline cellulose filler present extragranularly.

27. A process for preparing a tablet comprising at least about 50% w/w valaciclovir or a salt thereof, a binding agent, a microcrystalline cellulose filler, a lubricant selected from the group consisting of talc, sodium lauryl sulphate and alkaline earth metal stearate, and about 0.05 to 3.0% w/w colloidal silicon dioxide; wherein the hardness of the tablet is at least 9 kP, the friability is not more than 1%, and the ejection force is not more than 1000 N; said process comprising forming granules which include valaciclovir or a salt thereof and then blending the lubricant, colloidal silicon dioxide and at least a portion of the filler with said granules.

28. A process according to claim 26 comprising forming granules by mixing said valaciclovir or salt, optionally a binding agent or a portion thereof, and optionally a portion of the filler; granulating with a granulating solution to form granules or dissolving the binding agent or a portion in the granulating solution before adding to valaciclovir; drying the granules; blending the granules with the lubricant, colloidal silicon dioxide, and filler or a portion thereof; and then compressing the blended mixture to form a tablet.

* * * * *